US012582537B2

(12) United States Patent
Folan

(10) Patent No.: US 12,582,537 B2
(45) **Date of Patent: *Mar. 24, 2026**

(54) STENT WITH IMPROVED DEPLOYMENT CHARACTERISTICS

(71) Applicant: BOSTON SCIENTIFIC SCIMED, INC., Maple Grove, MN (US)

(72) Inventor: Martyn G. Folan, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 36 days.

This patent is subject to a terminal disclaimer.

(21) Appl. No.: 18/431,625

(22) Filed: Feb. 2, 2024

(65) Prior Publication Data

US 2024/0173153 A1     May 30, 2024

Related U.S. Application Data

(63) Continuation of application No. 17/539,366, filed on Dec. 1, 2021, now Pat. No. 11,918,496.

(Continued)

(51) Int. Cl.
*A61F 2/82*      (2013.01)
*A61F 2/86*      (2013.01)
*A61F 2/90*      (2013.01)

(52) U.S. Cl.
CPC .................. *A61F 2/90* (2013.01); *A61F 2/82* (2013.01); *A61F 2/86* (2013.01); *D10B 2509/06* (2013.01)

(58) Field of Classification Search
CPC ...... A61F 2/82; A61F 2/86; A61F 2/90; A61F 2230/0045; A61F 2230/0013; D10B 2509/06
See application file for complete search history.

(56) References Cited

U.S. PATENT DOCUMENTS 1,945,195 A     1/1934  Kellems
3,938,529 A     2/1976  Gibbons
          (Continued)

FOREIGN PATENT DOCUMENTS

CN     201108514 Y     9/2008
CN     201684049 U     12/2010
          (Continued)

OTHER PUBLICATIONS

International Search Report and Written opinion dated Oct. 9, 2018 for International Application No. PCT/US2018/043863.

(Continued)

*Primary Examiner* — Dinah Baria

(74) *Attorney, Agent, or Firm* — Seager, Tufte & Wickhem, LLP

(57)     ABSTRACT

A knitted stent extending along a central longitudinal axis may comprise a filament forming a plurality of cells arranged in a plurality of columns and a plurality of rows. The plurality of rows may extend parallel to the central longitudinal axis. The plurality of columns may extend circumferentially around the central longitudinal axis. The plurality of rows may include a plurality of loop rows and a plurality of rung rows interposed between adjacent loop rows. Each cell within the plurality of loop rows may include a circumferential loop element connected to two longitudinally oriented connector elements. The plurality of rung rows may include a plurality of circumferential rung elements connected to adjacent loop rows. A majority of the plurality of loop rows may include open cells having an open end. At least one of the plurality of loop rows may include a plurality of closed cells having a closed end.

20 Claims, 11 Drawing Sheets

Related U.S. Application Data

(60) Provisional application No. 63/120,402, filed on Dec. 2, 2020.

(56) References Cited

U.S. PATENT DOCUMENTS

| | | | |
|---|---|---|---|
| 5,064,435 A | 11/1991 | Porter | |
| 5,133,732 A | 7/1992 | Wiktor | |
| 5,167,614 A | 12/1992 | Tessmann et al. | |
| 5,234,456 A | 8/1993 | Silvestrini | |
| 5,238,004 A | 8/1993 | Sahatjian et al. | |
| 5,366,504 A | 11/1994 | Andersen et al. | |
| 5,383,927 A | 1/1995 | De Goicoechea et al. | |
| 5,607,464 A | 3/1997 | Trescony et al. | |
| 5,628,788 A | 5/1997 | Pinchuk | |
| 5,645,559 A | 7/1997 | Hachtman et al. | |
| 5,653,745 A | 8/1997 | Trescony et al. | |
| 5,662,713 A | 9/1997 | Andersen et al. | |
| 5,697,970 A | 12/1997 | Schmitt et al. | |
| 5,800,519 A | 9/1998 | Sandock | |
| 5,876,445 A | 3/1999 | Andersen et al. | |
| 5,984,965 A | 11/1999 | Knapp et al. | |
| 6,221,060 B1 | 4/2001 | Willard | |
| 6,240,978 B1 | 6/2001 | Gianotti | |
| 6,258,117 B1 | 7/2001 | Camrud et al. | |
| 6,264,689 B1 | 7/2001 | Colgan et al. | |
| 6,305,436 B1 | 10/2001 | Andersen et al. | |
| 6,358,275 B1 | 3/2002 | McIlroy et al. | |
| 6,416,537 B1 | 7/2002 | Martakos et al. | |
| 6,451,052 B1 | 9/2002 | Burmeister et al. | |
| 6,485,515 B2 | 11/2002 | Strecker | |
| 6,494,907 B1 | 12/2002 | Bulver | |
| 6,508,803 B1 | 1/2003 | Horikawa et al. | |
| 6,520,983 B1 | 2/2003 | Colgan et al. | |
| 6,540,773 B2 | 4/2003 | Dong | |
| 6,554,855 B1 | 4/2003 | Dong | |
| 6,652,577 B2 | 11/2003 | Gianotti | |
| 6,709,451 B1 | 3/2004 | Noble et al. | |
| 6,783,554 B2 | 8/2004 | Amara et al. | |
| 6,893,457 B2 | 5/2005 | Dong | |
| 6,939,372 B2 | 9/2005 | Dong | |
| 7,011,676 B2 | 3/2006 | Dong | |
| 7,169,139 B2 | 1/2007 | Teague et al. | |
| 7,195,646 B2 | 3/2007 | Nahleili | |
| 7,198,638 B2 | 4/2007 | Dong | |
| 7,338,530 B2 | 3/2008 | Carter et al. | |
| 7,364,587 B2 | 4/2008 | Dong et al. | |
| 7,594,928 B2 | 9/2009 | Headley, Jr. et al. | |
| D612,499 S | 3/2010 | Ondracek et al. | |
| 7,854,756 B2 | 12/2010 | Shaw | |
| 7,914,568 B2 | 3/2011 | Cully et al. | |
| 8,151,682 B2 | 4/2012 | Lilburn et al. | |
| 8,435,283 B2 | 5/2013 | Jordan et al. | |
| 8,435,285 B2 | 5/2013 | Shank et al. | |
| 8,454,675 B2 | 6/2013 | Houston et al. | |
| 8,753,407 B2 | 6/2014 | Nguyen | |
| 8,821,565 B2 | 9/2014 | Demetriades et al. | |
| 8,974,516 B2 | 3/2015 | Hyodoh et al. | |
| 9,265,635 B2 | 2/2016 | Walak | |
| 9,498,319 B2 | 11/2016 | Walak | |
| 9,839,508 B2 | 12/2017 | Walsh et al. | |
| 9,849,009 B2 | 12/2017 | Thompson | |
| 9,849,010 B2 | 12/2017 | Thompson | |
| 10,130,497 B2 | 11/2018 | Krautkremer et al. | |
| 2002/0022875 A1 | 2/2002 | Strecker | |
| 2002/0179166 A1 | 12/2002 | Houston et al. | |
| 2003/0040771 A1 | 2/2003 | Hyodoh et al. | |
| 2003/0040789 A1 | 2/2003 | Colgan et al. | |
| 2003/0093145 A1 | 5/2003 | Lawrence-Brown et al. | |
| 2003/0191517 A1 | 10/2003 | Osborne et al. | |
| 2004/0039435 A1 | 2/2004 | Hancock et al. | |
| 2004/0098099 A1 | 5/2004 | Mccullagh et al. | |
| 2004/0127973 A1 | 7/2004 | Mangiardi et al. | |
| 2004/0193141 A1 | 9/2004 | Leopold et al. | |
| 2005/0033418 A1 | 2/2005 | Banas et al. | |
| 2005/0049682 A1 | 3/2005 | Leanna et al. | |
| 2005/0154448 A1 | 7/2005 | Cully et al. | |
| 2005/0240278 A1 | 10/2005 | Aliski et al. | |
| 2005/0283962 A1 | 12/2005 | Boudjemline | |
| 2006/0265051 A1 | 11/2006 | Caro et al. | |
| 2007/0123969 A1 | 5/2007 | Gianotti | |
| 2007/0282453 A1 | 12/2007 | Weitzner et al. | |
| 2007/0299506 A1 | 12/2007 | Carter et al. | |
| 2008/0228262 A1 | 9/2008 | Goldmann et al. | |
| 2009/0005855 A1 | 1/2009 | Goto et al. | |
| 2009/0030363 A1 | 1/2009 | Gellman | |
| 2009/0043373 A1 | 2/2009 | Arnault De La Menardiere et al. | |
| 2009/0138070 A1 | 5/2009 | Holzer et al. | |
| 2009/0151416 A1 | 6/2009 | Obradovic et al. | |
| 2009/0187240 A1 | 7/2009 | Clerc et al. | |
| 2009/0276029 A1 | 11/2009 | Caro et al. | |
| 2010/0030321 A1 | 2/2010 | Mach | |
| 2010/0100170 A1 | 4/2010 | Tan et al. | |
| 2010/0191319 A1 | 7/2010 | Lilburn et al. | |
| 2010/0256731 A1 | 10/2010 | Mangiardi | |
| 2011/0082483 A1 | 4/2011 | Diamant et al. | |
| 2011/0213453 A1 | 9/2011 | Mangiardi | |
| 2011/0307070 A1 | 12/2011 | Clerc et al. | |
| 2012/0116528 A1 | 5/2012 | Nguyen | |
| 2012/0165956 A1 | 6/2012 | Li | |
| 2012/0290100 A1 | 11/2012 | Li | |
| 2012/0296257 A1 | 11/2012 | Van Dam et al. | |
| 2013/0018452 A1 | 1/2013 | Weitzner et al. | |
| 2013/0172983 A1 | 7/2013 | Clerc et al. | |
| 2014/0243992 A1 | 8/2014 | Walsh et al. | |
| 2014/0277560 A1 | 9/2014 | Walak | |
| 2014/0277561 A1 | 9/2014 | Jordan | |
| 2014/0343683 A1 | 11/2014 | Jeon et al. | |
| 2015/0282955 A1 | 10/2015 | Guler et al. | |
| 2016/0058585 A1 | 3/2016 | Seddon et al. | |
| 2016/0100930 A1 | 4/2016 | Walsh et al. | |
| 2016/0213498 A1 | 7/2016 | Wang | |
| 2019/0029850 A1 | 1/2019 | Keating et al. | |
| 2019/0307586 A1 | 10/2019 | Gilmartin et al. | |
| 2020/0214858 A1 | 7/2020 | Gilmartin et al. | |

FOREIGN PATENT DOCUMENTS

| | | | |
|---|---|---|---|
| CN | 102362023 A2 | 2/2012 | |
| DE | 102013221450 A1 | 7/2014 | |
| EP | 1258229 A1 | 11/2002 | |
| GB | 2512176 A | 9/2014 | |
| JP | 2005168757 A | 6/2005 | |
| KR | 20110119743 A | 11/2011 | |
| KR | 20140094144 A | 7/2014 | |
| WO | 2008076706 A2 | 6/2008 | |
| WO | 2010085794 A2 | 7/2010 | |
| WO | 2014134352 A1 | 9/2014 | |
| WO | 2014164308 A1 | 10/2014 | |

OTHER PUBLICATIONS

International Search Report and Written Opinion dated Aug. 29, 2019 for International Application No. PCT/US2019/026407.

International Search Report and Written Opinion dated Mar. 19, 2020 for International Application No. PCT/US2020/0121373.

Machine translation of JP2005169757, pp. 1-4, accessed Aug. 26, 2021. https://wordwide.espacenet.com/patent/search/family/034732792/publication/JP2005168757A?q=pn%3DJP2005168757A (Year: 2021).

International Search Report and Written Opinion dated Mar. 29, 2022 for International Application No. PCT/US2021/061348.

STENT WITH IMPROVED DEPLOYMENT CHARACTERISTICS

CROSS REFERENCE TO RELATED APPLICATIONS

This application is a continuation of U.S. patent application Ser. No. 17/539,366, filed Dec. 1, 2021, which claims the benefit of and priority to U.S. Provisional Patent Application Ser. No. 63/120,402 filed on Dec. 2, 2020, the disclosure of which is incorporated herein by reference.

TECHNICAL FIELD

The present disclosure pertains to medical devices, methods for manufacturing medical devices, and uses thereof. More particularly, the present disclosure pertains to a stent for implantation in a body lumen, and associated methods.

BACKGROUND

Implantable medical devices (e.g., expandable stents) may be designed to treat a variety of medical conditions in the body. For example, some expandable stents may be designed to radially expand and support a body lumen and/or provide a fluid pathway for digested material, blood, or other fluid to flow therethrough following a medical procedure. Some medical devices may include radially or self-expanding stents which may be implanted transluminally via a variety of medical device delivery systems. These stents may be implanted in a variety of body lumens such as coronary or peripheral arteries, the esophageal tract, gastrointestinal tract (including the intestine, stomach and the colon), tracheobronchial tract, urinary tract, biliary tract, vascular system, etc.

In some instances it may be desirable to design stents to include sufficient flexibility while maintaining sufficient radial force to open the body lumen at the treatment site. In some instances, the radial force may aid in anchoring the stent and preventing migration within the lumen. In some instances, different stent configurations may provide different deliverability, flexibility, radial force/strength, and/or anchoring characteristics. For example, knitted stents may be considered to possess superior flexibility and/or radial strength characteristics. However, knitted stents do not easily lend themselves to re-constrainment and/or repositioning.

In some instances, a knitted stent may be the most appropriate or desirable type of stent for a particular lumen or use—for example, in gastrointestinal and/or tracheobronchial anatomy. However, delivery and implantation of knitted stents may be challenging if the stent is not sized properly. In some instances, a phenomenon known as a "C-fold" may develop if the target lumen and/or vessel is smaller than that specified for the stent and/or if the stent is too large for the target lumen and/or vessel. A "C-fold" may cause and/or promote incomplete stricture resolution, stent migration, food and/or fluid impaction on the lumen wall, and/or lumen blockage.

There is an ongoing need to provide alternative stent configurations and/or methods with improved deliverability characteristics which avoid and/or prevent the formation of a "C-fold".

SUMMARY

In one example, a knitted stent extending along a central longitudinal axis may comprise a filament forming a plurality of cells arranged in a plurality of columns and a plurality of rows. The plurality of rows may extend parallel to the central longitudinal axis from a first end of the knitted stent to a second end of the knitted stent. The plurality of columns may extend circumferentially around the central longitudinal axis. The plurality of rows may include a plurality of loop rows and a plurality of rung rows interposed between adjacent loop rows. Each cell within the plurality of loop rows may include a circumferential loop element connected to two longitudinally oriented connector elements. The plurality of rung rows may include a plurality of circumferential rung elements connected to adjacent loop rows. A majority of the plurality of loop rows may include open cells having an open end disposed between the two longitudinally oriented connector elements and opposite the circumferential loop element. At least one of the plurality of loop rows may include a plurality of closed cells having a closed end formed by crossing the two longitudinally oriented connector elements at a position opposite the circumferential loop element.

In addition or alternatively to any example disclosed herein, the circumferential loop element of each cell is oriented toward the first end of the knitted stent.

In addition or alternatively to any example disclosed herein, the plurality of closed cells is disposed proximate the first end or the second end of the knitted stent.

In addition or alternatively to any example disclosed herein, the plurality of circumferential rung elements is connected at opposite ends to one of the two longitudinally oriented connector elements from each adjacent loop row.

In addition or alternatively to any example disclosed herein, the at least one of the plurality of loop rows includes a first portion of a first loop row and a second portion of the first loop row spaced apart longitudinally from the first portion, wherein the first portion includes a first plurality of closed cells and the second portion includes a second plurality of closed cells.

In addition or alternatively to any example disclosed herein, the first plurality of closed cells is arranged immediately adjacent to each other along the central longitudinal axis and the second plurality of closed cells is arranged immediately adjacent to each other along the central longitudinal axis.

In addition or alternatively to any example disclosed herein, the first portion of the first loop row is disposed within a first end portion of the knitted stent and the second portion of the first loop row is disposed within a second end portion of the knitted stent, wherein the first end portion and the second end portion are spaced apart by a body portion of the knitted stent.

In addition or alternatively to any example disclosed herein, in a radially expanded configuration of the knitted stent, the first end portion has a first outer diameter greater than an outer diameter of the body portion.

In addition or alternatively to any example disclosed herein, in a radially expanded configuration of the knitted stent, the second end portion has a second outer diameter greater than an outer diameter of the body portion.

In addition or alternatively to any example disclosed herein, the at least one of the plurality of loop rows includes a first loop row extending from the first end of the knitted stent to the second end of the knitted stent, wherein the plurality of closed cells is arranged immediately adjacent to each other from the first end of the knitted stent to the second end of the knitted stent within the first loop row.

In addition or alternatively to any example disclosed herein, the at least one of the plurality of loop rows further includes a second loop row extending from the first end of the knitted stent to the second end of the knitted stent, the second loop row being circumferentially spaced apart from the first loop row. The second loop row includes a plurality of closed cells arranged immediately adjacent to each other from the first end of the knitted stent to the second end of the knitted stent within the second loop row.

In addition or alternatively to any example disclosed herein, every closed cell of the knitted stent is disposed within a single loop row.

In addition or alternatively to any example disclosed herein, a knitted stent extending along a central longitudinal axis may comprise a filament forming a plurality of cells arranged in a plurality of columns and a plurality of rows. The plurality of rows may extend parallel to the central longitudinal axis from a first end of the knitted stent to a second end of the knitted stent. The plurality of columns may extend circumferentially around the central longitudinal axis. The plurality of rows may include a plurality of loop rows and a plurality of rung rows interposed between adjacent loop rows. Each cell within the plurality of loop rows may include a circumferential loop element connected to two longitudinally oriented connector elements. The plurality of rung rows may include a plurality of circumferential rung elements having opposite ends connected to adjacent loop rows. The knitted stent may include a first end portion, a second end portion, and a body portion disposed between the first end portion and the second end portion. In a radially expanded configuration, the first end portion and the second end portion may each have an outer diameter that is greater than an outer diameter of the body portion. Within the body portion, the plurality of loop rows may be formed from open cells having an open end disposed between the two longitudinally oriented connector elements and opposite the circumferential loop element. Within the first end portion, at least one of the plurality of loop rows may include a first plurality of closed cells having a closed end formed by crossing the two longitudinally oriented connector elements at a position opposite the circumferential loop element. Within the second end portion, at least one of the plurality of loop rows may include a second plurality of closed cells having a closed end formed by crossing the two longitudinally oriented connector elements at a position opposite the circumferential loop element.

In addition or alternatively to any example disclosed herein, a sum of the plurality of cells of the plurality of loop rows in the first end portion, the second end portion, and the body portion comprises at least 90% open cells.

In addition or alternatively to any example disclosed herein, the first plurality of closed cells extends from the body portion to the first end of the knitted stent and the second plurality of closed cells extends from the body portion to the second end of the knitted stent.

In addition or alternatively to any example disclosed herein, the first plurality of closed cells exerts a first circumferential force on the first end portion of the knitted stent and the second plurality of closed cells exerts a second circumferential force on the second end portion of the knitted stent.

In addition or alternatively to any example disclosed herein, every closed cell of the knitted stent is disposed within a single loop row.

In addition or alternatively to any example disclosed herein, a knitted stent extending along a central longitudinal axis may comprise a filament forming a plurality of cells arranged in a plurality of columns and a plurality of rows. The plurality of rows may extend parallel to the central longitudinal axis from a first end of the knitted stent to a second end of the knitted stent. The plurality of columns may extend circumferentially around the central longitudinal axis. The plurality of rows may include a plurality of loop rows and a plurality of rung rows interposed between adjacent loop rows. Each cell within the plurality of loop rows may include a circumferential loop element connected to two longitudinally oriented connector elements. The plurality of rung rows may include a plurality of circumferential rung elements connected to adjacent loop rows. A majority of the plurality of loop rows may include open cells having an open end disposed between the two longitudinally oriented connector elements and opposite the circumferential loop element. At least one of the plurality of loop rows may include a plurality of closed cells having a closed end formed by crossing the two longitudinally oriented connector elements at a position opposite the circumferential loop element. The plurality of closed cells may be longitudinally spaced apart from each other within the at least one of the plurality of loop rows.

In addition or alternatively to any example disclosed herein, each consecutive pair of the plurality of closed cells is spaced longitudinally apart from each other by one open cell within the at least one of the plurality of loop rows.

In addition or alternatively to any example disclosed herein, each consecutive pair of the plurality of closed cells is spaced longitudinally apart from each other by two open cells within the at least one of the plurality of loop rows.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 4 is an end view of a knitted stent disposed within a body lumen that is smaller than the knitted stent is designed for;

Figure 1:
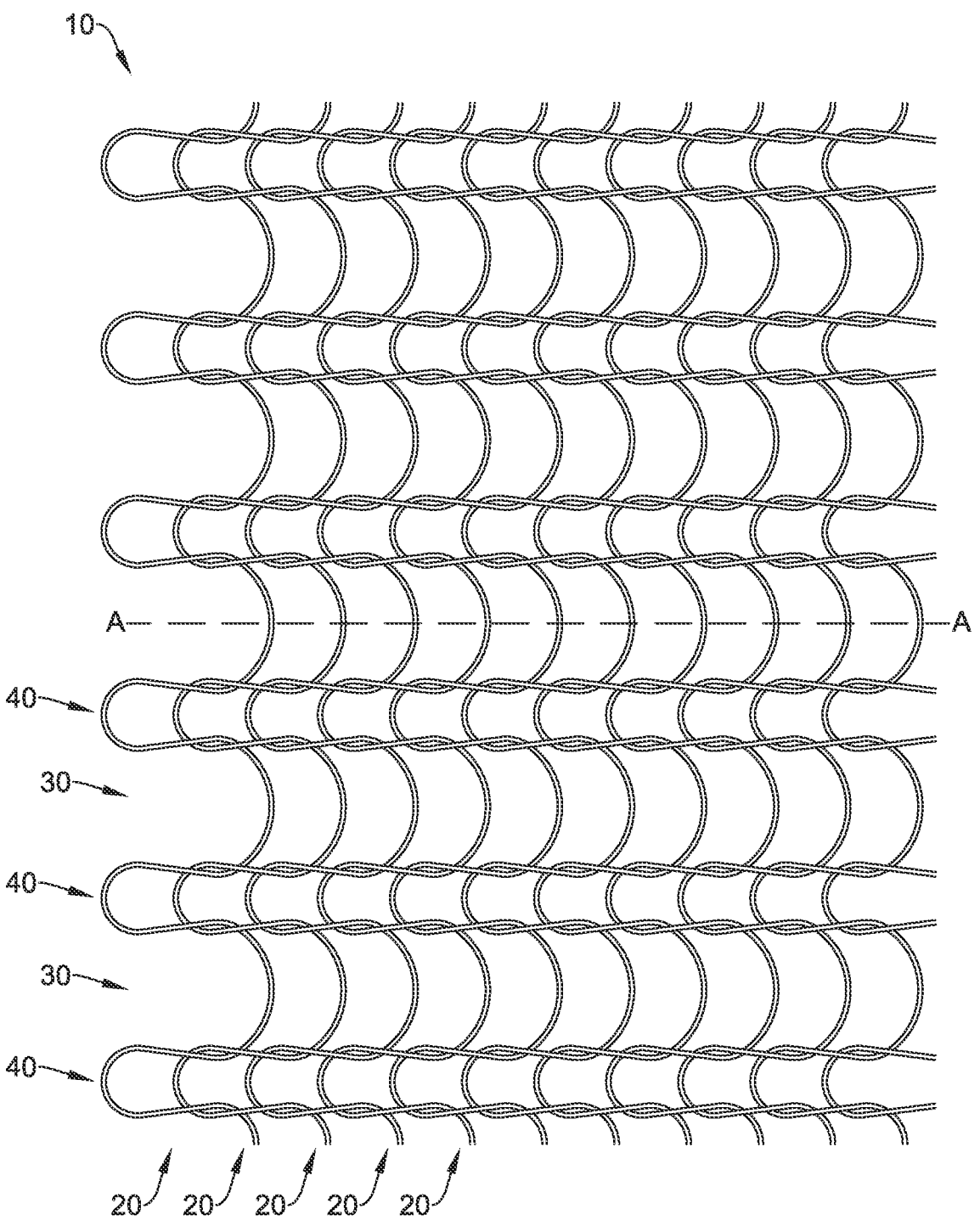
FIG. 1 is an illustration of a portion of a knitted stent having an open loop construction in a flat pattern view.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claims. Those skilled in the art will recognize that the various elements described and/or shown may be arranged in various combinations and configurations without departing from the scope of the disclosure. The detailed description and drawings illustrate example embodiments of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosure. Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures illustrate selected components and/or arrangements of an endoprosthesis or stent. It should be noted that in any given figure, some features of the endoprosthesis or stent may not be shown, or may be shown schematically, for simplicity. Additional details regarding some of the components of the endoprosthesis or stent may be illustrated in other figures in greater detail. It is to be noted that in order to facilitate understanding, certain features of the disclosure may be described in the singular, even though those features may be plural or recurring within the disclosure. Each instance of the features may include and/or be encompassed by the singular disclosure(s), unless expressly stated to the contrary. For example, a reference to "the filament", "the cell", "the strut", or other features may be equally referred to all instances and quantities beyond one of said feature. As such, it will be understood that the following discussion may apply equally to any and/or all of the components for which there are more than one within the endoprosthesis or stent, unless explicitly stated to the contrary. Additionally, not all instances of some elements or features may be shown in each figure for clarity.

FIG. 1 illustrates a flat pattern view of a conventional knitted stent 10 according to one known example. The knitted stent 10 may be of a basic self-expanding configuration having a plurality of open-ended loops interlaced together. Conventional knitted self-expanding stents are generally designed using an automated weft knitting process that produces parallel columns 20 of knit stitches that are oriented generally perpendicular to a central longitudinal axis A-A of the stent in both an expanded, relaxed configuration and an elongated, constrained configuration, and parallel rows 30 and 40 of knit stitches that are oriented parallel to the central longitudinal axis of the stent in both the expanded, relaxed configuration and the elongated, constrained configuration. The parallel rows 40 are generally smaller and/or tighter than the parallel rows 30. Conventional knitted stents have certain advantages and disadvantages. For example, the knitted stent 10 may provide good radial strength with minimal foreshortening which may be desirable in esophageal and tracheobronchial applications as well as some post-bariatric surgery applications. However, the knitted stent 10 may be difficult to constrain, especially into a coaxial delivery system and thus may be delivered using a system which may not offer a method of recapture, such as a crochet delivery system.

Figure 2:
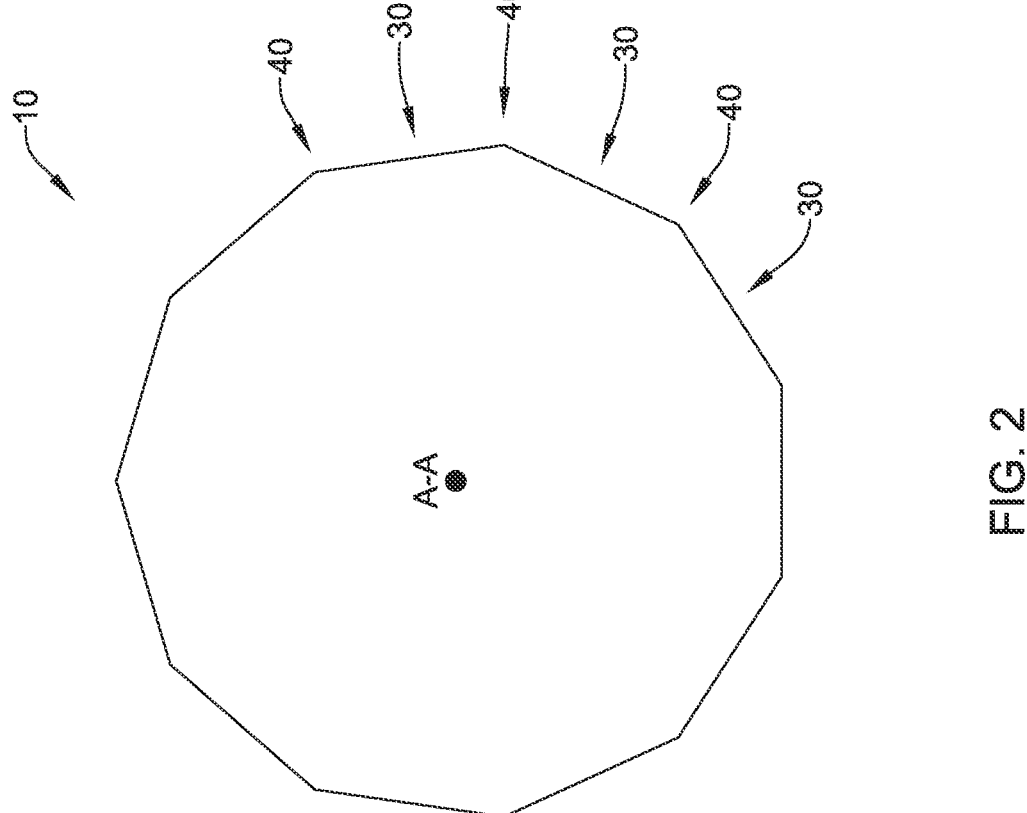
FIG. 2 is an end view of a knitted stent.

FIG. 2 schematically illustrates an end view of the knitted stent 10. In practice, the knitted stent 10 may have a generally circular cross-sectional shape. However, as may be seen in FIG. 2, if/when the parallel rows 30 form as straight legs, the parallel rows 30 form "sides" of a polygon-shaped stent structure and the parallel rows 40 form "corners" of the polygon-shaped stent structure. The parallel rows 30 may be disposed circumferentially between adjacent parallel rows 40 and/or the parallel rows 40 may be disposed circumferentially between adjacent parallel rows 30. While the parallel rows 40 do not form perfectly angular corners, the illustration shows how the parallel rows 30 would be positioned at an angle relative to each other if they were formed as straight legs. In practice, the parallel rows 30 are curved radially outward, thus giving the knitted stent a more circular shape. When the knitted stent 10 expands, its rung elements (e.g., the parallel rows 30) are bounded at each end where its loop elements (e.g., the parallel rows 40) are formed such that each rung element behaves in isolation from its neighboring rung elements and permitting the rung elements to react to constrainment resistance in its own locality.

Figure 3:
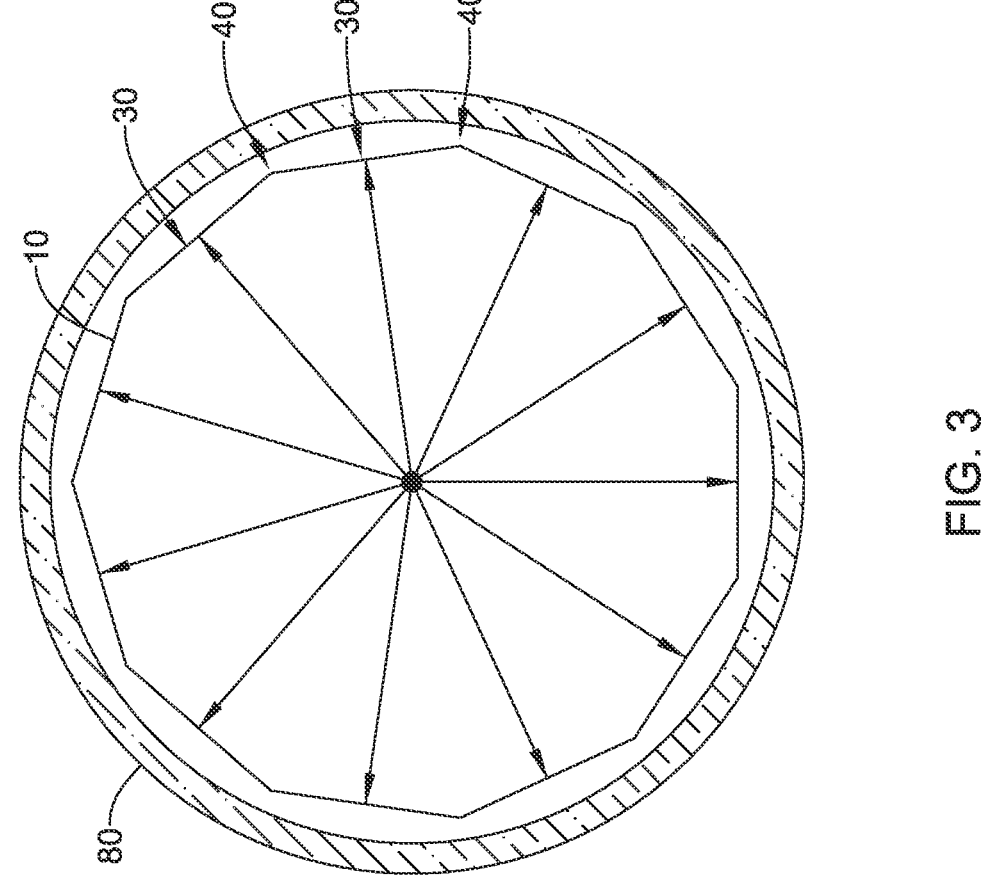
FIG. 3 is an end view of a properly sized knitted stent disposed within a body lumen.

FIG. 3 schematically illustrates the knitted stent 10 in the radially expanded configuration when properly sized for positioning within a body lumen 80. With conventional knitted stents, when properly sized to the body lumen, the parallel rows 30 and the parallel rows 40 cooperate to expand evenly around the circumference of the body lumen 80. In general, each rung element (e.g., "side" or parallel row 30) of the stent can expand with equal radial force without resistance and the knitted stent 10 may demonstrate an efficient circular cross-section in the radially expanded configuration. When the knitted stent 10 is deployed, the loop elements (e.g., the parallel rows 40) try to axially shorten, thus pushing filament material into the adjoining rung elements to expand radially and increase the outer diameter of the knitted stent 10 up to the diameter of the body lumen 80.

Figure 4:
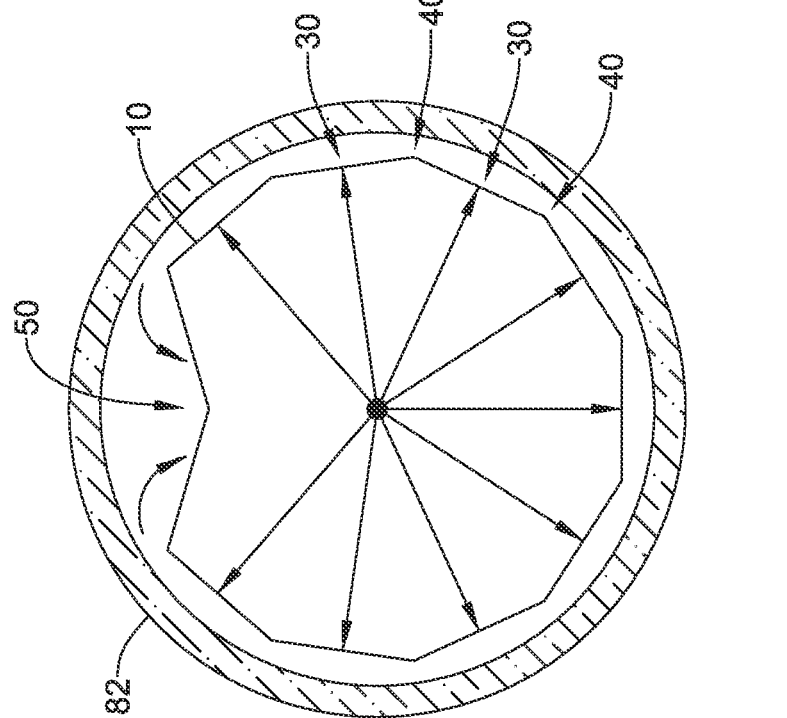

FIG. 4 schematically illustrates the effect of an undersized body lumen 82 for the same knitted stent 10, or in the alternative, the effect of the knitted stent 10 being improperly sized larger than the body lumen 82. As the knitted stent 10 is deployed from a crochet delivery device, resistance to expansion of the knitted stent 10 is reduced upon individual rung elements (e.g., the parallel rows 30) in an ordered fashion running in a clockwise (or counterclockwise) manner. As a result of the way the knitted stent 10 is delivered, not all of the rung elements are in a position to expand radially at the same time. This inequality allows for the initially released rung elements to begin expanding into their local space while later rung elements must wait for resistance from the delivery device to be removed. The rung elements all maintain or attempt to maintain their respective expanded size upon being released. In the example of FIG. 4, this unequal expansion results in the formation of the "C-fold" 50 as the last rung elements are not in a position to expand due to the lack of space within the body lumen 82 and increased resistance from the rung elements that have already expanded into position against the wall of the body lumen 82. As the relative size difference between the body lumen 82 and the knitted stent 10 increases (e.g., the body lumen 82 gets smaller relative to the knitted stent 10, or the knitted stent 10 gets larger relative to the body lumen 82), the process becomes exaggerated and the severity of the "C-fold" 50 may become worse. Once the knitted stent 10 has expanded into this arrangement (e.g., has formed the "C-fold" 50), reversing the situation may be difficult or impossible, particularly in situ.

An alternative self-expanding knitted stent is desired that is capable of overcoming the conditions that permit a "C-fold" to form and/or allow the knitted stent to be more adaptable to a wider range of body lumen diameters. While the embodiments disclosed herein are discussed with reference to esophageal and tracheobronchial stents, it is contemplated that the stents described herein may be used and sized for use in other locations such as, but not limited to: bodily tissue, bodily organs, vascular lumens, non-vascular lumens, and combinations thereof, such as, but not limited to, in the coronary or peripheral vasculature, trachea, bronchi, colon, small intestine, biliary tract, urinary tract, prostate, brain, stomach, and the like.

Figure 5:
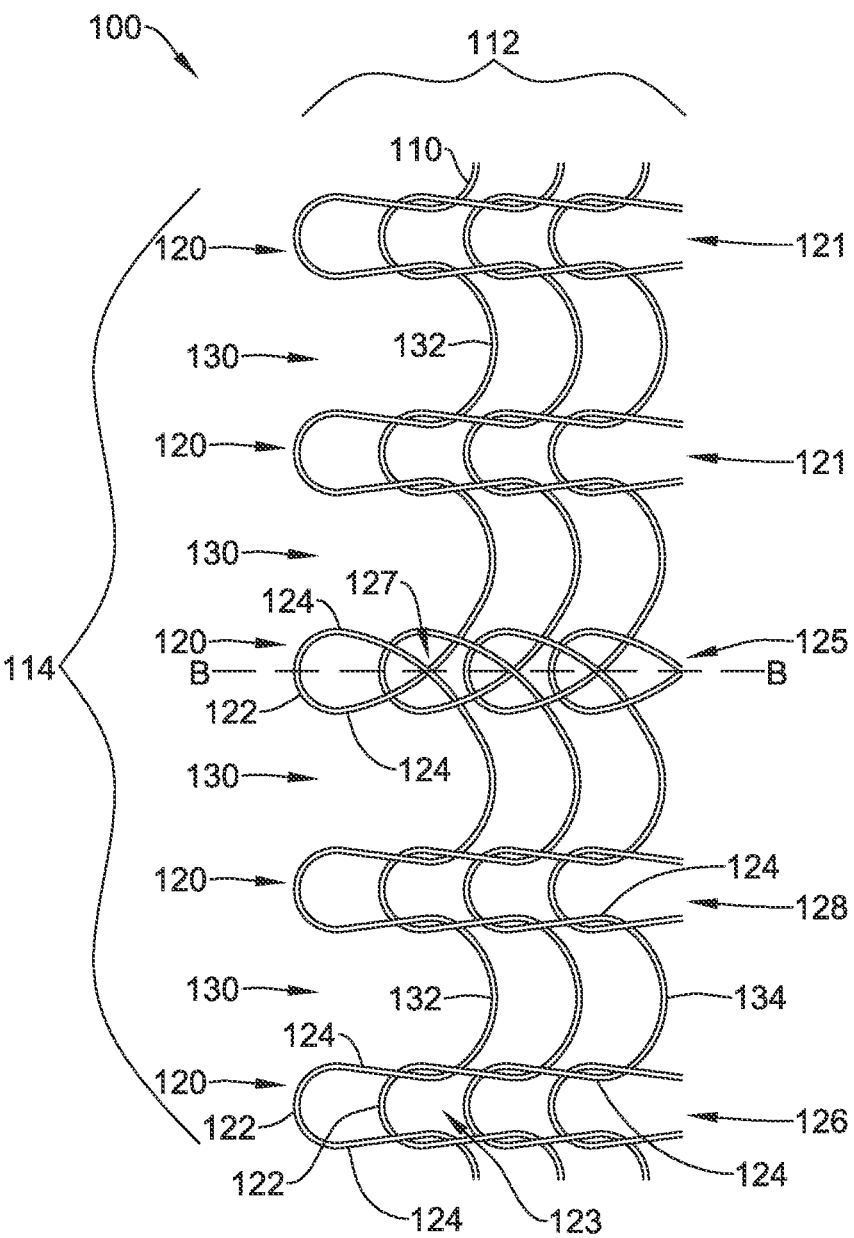
FIG. 5 is an illustration of a portion of a knitted stent including a row of twisted loops in a flat pattern view.

FIG. 5 illustrates a flat pattern view of a portion of a knitted stent 100 configured according to the present disclosure. The knitted stent 100 may form a tubular member extending along a central longitudinal axis B-B from a first end of the knitted stent 100 to a second end of the knitted stent 100. The knitted stent 100 may be configured to shift from a radially collapsed configuration to a radially expanded configuration upon deployment. For example, the tubular member may be self-expanding from a compressed diameter during delivery to an expanded diameter when unconstrained by a constraining member surrounding the tubular member. The knitted stent 100 may include a lumen extending from the first end to the second end to allow for the passage of fluids, food, etc. The knitted stent 100 may include and/or may be formed from a filament 110 forming a plurality of cells arranged in a plurality of columns 112 and a plurality of rows 114. In some embodiments, the knitted stent 100 may be formed from only a single filament interwoven and/or interlaced with itself to form the plurality of cells. In some embodiments, the filament 110 may be a monofilament, while in other embodiments the filament 110 may be two or more filaments. In some embodiments, an inner and/or outer surface of the knitted stent 100 may be entirely, substantially, or partially, covered with a polymeric covering or coating. The polymeric covering or coating may extend across and/or occlude one or more of the plurality of cells formed and/or defined by the filament 110. The polymeric covering or coating may help reduce food impaction and/or tumor or tissue ingrowth. In some embodiments, the knitted stent 100 may include a one-way valve (not shown), such as an elastomeric slit valve or a duck bill valve, positioned within the lumen thereof to prevent retrograde flow of fluids.

The plurality of rows 114 may extend parallel to the central longitudinal axis B-B from the first end of the knitted stent 100 to the second end of the knitted stent 100. The plurality of columns 112 may extend circumferentially around the central longitudinal axis B-B. It is noted that when knitted from a single filament, each column 112 may extend circumferentially around the central longitudinal axis B-B in a slightly helical direction, such that at each complete revolution an adjacent column 112 is formed. In some embodiments, the plurality of columns 112 may be oriented perpendicular to the central longitudinal axis B-B. The plurality of rows may include a plurality of loop rows 120 and a plurality of rung rows 130 interposed between adjacent loop rows 120. Thus, the loop rows 120 may alternate with the rung rows 130 around the circumference of the tubular member. Each circumferentially adjacent and/or consecutive pair of the plurality of loops rows 120 may be spaced apart circumferentially from each other by one of the plurality of rung rows 130. Each cell within the plurality of loop rows 120 may include a circumferential loop element 122 connected to two longitudinally oriented connector elements 124, wherein the circumferential loop element 122 is oriented generally circumferentially around the central longitudinal axis B-B. The circumferential loop element 122 of each cell may be oriented and/or positioned toward the first end of the knitted stent 100 within its respective cell. The plurality of rung rows 130 may each include a plurality of circumferential rung elements 132 connected to adjacent loop rows 120, wherein the plurality of circumferential rung elements 132 is oriented generally circumferentially around the central longitudinal axis B-B. Each of the plurality of circumferential rung elements 132 may be connected at opposite ends to one of the two longitudinally oriented connector elements 124 from each adjacent loop row 120. For example, one circumferential rung element 134 may be connected at a first end to one of the two longitudinally oriented connector elements 124 from a first loop row 126 and connected at a second end to one of the two longitudinally oriented connector elements 124 from a second loop row 128 disposed circumferentially adjacent to the first loop row 126 (and spaced circumferentially apart from the first loop row 126 by the rung row 130 that includes the circumferential rung element 134). In some embodiments, the plurality of circumferential rung elements 132 may be between about 0.1 millimeters and about 10.0 millimeters in length in the radially expanded configuration. In other examples, the plurality of circumferential rung elements 132 may have a length between 1 millimeters and 5 millimeters. In still other examples, the plurality of circumferential rung elements 132 may have a length between 2 millimeters and 3 millimeters.

A majority of the plurality of loop rows 120 includes open cells 121 each having an open end 123 disposed between the two longitudinally oriented connector elements 124 at a position opposite the circumferential loop element 122. Accordingly, the plurality of open cells 121 may alternatively and/or interchangeably be referred to as "open loops" or "standard loops". In some embodiments, at least one of the plurality of loop rows 120 includes a plurality of closed cells 125 each having a closed end 127 formed by twisting or crossing the two longitudinally oriented connector elements 124 at a position opposite the circumferential loop element 122. Accordingly, the plurality of closed cells 125 may alternatively and/or interchangeably be referred to as "twisted loops". In some embodiments, the plurality of closed cells 125 may be disposed proximate the first end or the second end of the knitted stent 100. In some embodiments, the plurality of closed cells 125 may be disposed proximate the first end and the second end of the knitted stent 100. In some embodiments, every closed cell 125 of the knitted stent 100 may be disposed within a single loop row 120. In some embodiments, the plurality of closed cells 125 may be arranged immediately adjacent to each other along the central longitudinal axis B-B from the first end of the knitted stent 100 to the second end of the knitted stent 100 within the single loop row 120. Each of the two longitudinally oriented connector elements 124 forming each of the plurality of closed cells 125 may be directly connected to one circumferential rung element 132 from each adjacent rung row 130.

When the knitted stent 100 having the plurality of closed cells 125 (e.g., the twisted loops) as described herein is deployed, the two longitudinally oriented connector elements 124 of each of the open cells 121 (e.g., the standard loops) axially shorten, thereby pushing the filament material into the adjoining and/or directly connected rung elements 132 to radially expand the knitted stent 100. The plurality of closed cells 125 is configured and/or able to accept and/or absorb the extra filament material from the two longitudinally oriented connector elements 124 of the adjacent loop rows 120. Similarly, the plurality of closed cells 125 (e.g., the twisted loops) may be configured to elongate and/or deform longitudinally when receiving filament material from the two directly connected circumferential rung elements 132 and/or the two longitudinally oriented connector elements 124 of the adjacent loop rows 120, allowing the diameter of the knitted stent 100 to be achieved without a "C-fold" forming. As such, the plurality of closed cells 125 may act as a suspension feature within the knitted stent 100 permitting the knitted stent 100 to flex and/or self-adjust when the knitted stent 100 is incorrectly sized with respect to the body lumen. In at least some embodiments, the plurality of closed cells 125 may be positioned and/or configured to open and/or be released last during deployment of the knitted stent 100 in order to optimize and/or maximize the adaptability of the knitted stent 100 to changing body lumen diameters because the plurality of closed cells 125 (e.g., the twisted loops) can elongate by differing amounts depending upon the discrepancy between the designed and/or labeled outer diameter of the knitted stent 100 and the inner diameter of the target body lumen.

Figure 6:
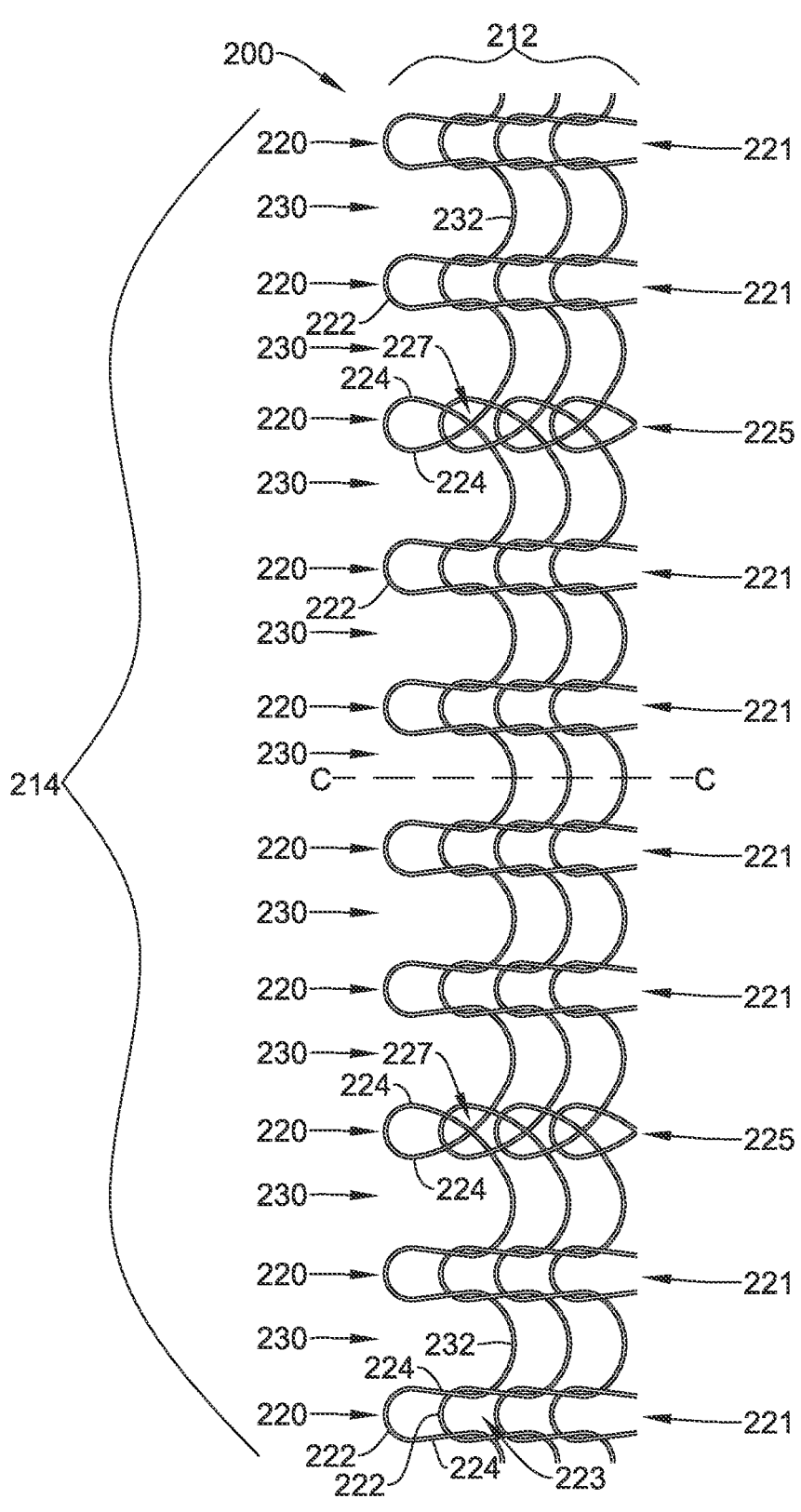
FIG. 6 is an illustration of a portion of a knitted stent including a plurality of rows of twisted loops in a flat pattern view.

FIG. 6 illustrates a flat pattern view of an alternative configuration of a knitted stent 200 similar to the knitted stent 100. As such, many characteristics and/or advantages are the same. The knitted stent 200 may form a tubular member extending along a central longitudinal axis C-C from a first end of the knitted stent 200 to a second end of the knitted stent 200. The knitted stent 200 may be configured to shift from a radially collapsed configuration to a radially expanded configuration upon deployment. For example, the tubular member may be self-expanding from a compressed diameter during delivery to an expanded diameter when unconstrained by a constraining member surrounding the tubular member. The knitted stent 200 may include a lumen extending from the first end to the second end to allow for the passage of fluids, food, etc. The knitted stent 200 may include and/or may be formed from a filament forming a plurality of cells arranged in a plurality of columns 212 and a plurality of rows 214. In some embodiments, the knitted stent 200 may be formed from only a single filament interwoven and/or interlaced with itself to form the plurality of cells. In some embodiments, the filament may be a monofilament, while in other embodiments the filament may be two or more filaments. In some embodiments, an inner and/or outer surface of the knitted stent 200 may be entirely, substantially, or partially, covered with a polymeric covering or coating. The polymeric covering or coating may extend across and/or occlude one or more of the plurality of cells formed and/or defined by the filament. The polymeric covering or coating may help reduce food impaction and/or tumor or tissue ingrowth. In some embodiments, the knitted stent 200 may include a one-way valve (not shown), such as an elastomeric slit valve or a duck bill valve, positioned within the lumen thereof to prevent retrograde flow of fluids.

The plurality of rows 214 may extend parallel to the central longitudinal axis C-C from the first end of the knitted stent 200 to the second end of the knitted stent 200. The plurality of columns 212 may extend circumferentially around the central longitudinal axis C-C. It is noted that when knitted from a single filament, each column 212 may extend circumferentially around the central longitudinal axis C-C in a slightly helical direction, such that at each complete revolution an adjacent column 212 is formed. In some embodiments, the plurality of columns 212 may be oriented perpendicular to the central longitudinal axis C-C. The plurality of rows may include a plurality of loop rows 220 and a plurality of rung rows 230 interposed between adjacent loop rows 220. Thus, the loop rows 220 may alternate with the rung rows 230 around the circumference of the tubular member. Each circumferentially adjacent and/or consecutive pair of the plurality of loops rows 220 may be spaced apart circumferentially from each other by one of the plurality of rung rows 230. Each cell within the plurality of loop rows 220 may include a circumferential loop element 222 connected to two longitudinally oriented connector elements 224, wherein the circumferential loop element 222 is oriented generally circumferentially around the central longitudinal axis C-C. The circumferential loop element 222 of each cell may be oriented and/or positioned toward the first end of the knitted stent 200 within its respective cell. The plurality of rung rows 230 may each include a plurality of circumferential rung elements 232 connected to adjacent loop rows 220, wherein the plurality of circumferential rung elements 232 is oriented generally circumferentially around the central longitudinal axis C-C. Each of the plurality of circumferential rung elements 232 may be connected at opposite ends to one of the two longitudinally oriented connector elements 224 from each adjacent loop row 220. For example, one circumferential rung element 232 may be connected at a first end to one of the two longitudinally oriented connector elements 224 from one loop row and connected at a second end to one of the two longitudinally oriented connector elements 224 from another loop row disposed circumferentially adjacent to the one loop row (and spaced circumferentially apart from the one loop row 220 by the rung row 230 that includes the circumferential rung element 232).

A majority of the plurality of loop rows 220 includes open cells 221 each having an open end 223 disposed between the two longitudinally oriented connector elements 224 at a position opposite the circumferential loop element 222. Accordingly, the plurality of open cells 221 may alternatively and/or interchangeably be referred to as "open loops" or "standard loops". In some embodiments, at least one of the plurality of loop rows 220 includes a plurality of closed cells 225 each having a closed end 227 formed by twisting or crossing the two longitudinally oriented connector elements 224 at a position opposite the circumferential loop element 222. Accordingly, the plurality of closed cells 225 may alternatively and/or interchangeably be referred to as "twisted loops". In some embodiments, the at least one of the plurality of loop rows 220 including the plurality of closed cells 225 may include a first loop row and a second loop row circumferentially spaced apart from the first loop row 220. In some embodiments, the first loop row and the second loop row may be disposed on circumferentially opposing portions of the knitted stent 200. For example, in some embodiments, the first loop row may be circumferentially and/or radially offset from the second loop row, when measured circumferentially and/or radially around the central longitudinal axis C-C, by about 140 degrees, about 150 degrees, about 160 degrees, about 162 degrees, about 168 degrees, about 170 degrees, about 180 degrees, about 189 degrees, about 190 degrees, about 192 degrees, about 198 degrees, about 200 degrees, about 210 degrees, about 220 degrees, or another suitable angle depending upon the number of loop rows present in the knitted stent 200.

In some embodiments, the plurality of closed cells 225 may be disposed proximate the first end or the second end of the knitted stent 200. In some embodiments, the plurality of closed cells 225 may be disposed proximate the first end and the second end of the knitted stent 200. In at least some embodiments, the plurality of closed cells 225 may extend from the first end of the knitted stent 200 to the second end of the knitted stent 200. In some embodiments, the plurality of closed cells 225 may be arranged immediately adjacent to each other along the central longitudinal axis C-C from the first end of the knitted stent 200 to the second end of the knitted stent 200 within the first loop row and/or the second loop row. Each of the two longitudinally oriented connector elements 224 forming each of the plurality of closed cells 225 may be directly connected to one circumferential rung element 232 from each adjacent rung row 230.

When the knitted stent 200 having the plurality of closed cells 225 (e.g., the twisted loops) as described herein is deployed, the two longitudinally oriented connector elements 224 of each of the open cells 221 (e.g., the standard loops) axially shorten, thereby pushing the filament material into the adjoining and/or directly connected rung elements 232 to radially expand the knitted stent 200. The plurality of closed cells 225 is configured and/or able to accept and/or absorb the extra filament material from the two longitudinally oriented connector elements 224 of the adjacent loop rows 220. Similarly, the plurality of closed cells 225 (e.g., the twisted loops) may be configured to elongate and/or deform longitudinally when receiving filament material from the two directly connected circumferential rung elements 232 and/or the two longitudinally oriented connector elements 224 of the adjacent loop rows 220, allowing the diameter of the knitted stent 200 to be achieved without a "C-fold" forming. As such, the plurality of closed cells 225 may act as a suspension feature within the knitted stent 200 permitting the knitted stent 200 to flex and/or self-adjust when the knitted stent 200 is incorrectly sized with respect to the body lumen. In at least some embodiments, the plurality of closed cells 225 may be positioned and/or configured to open and/or be released last during deployment of the knitted stent 200 in order to optimize and/or maximize the adaptability of the knitted stent 200 to changing body lumen diameters because the plurality of closed cells 225 (e.g., the twisted loops) can elongate by differing amounts depending upon the discrepancy between the designed and/or labeled outer diameter of the knitted stent 200 and the inner diameter of the target body lumen.

Figure 7:
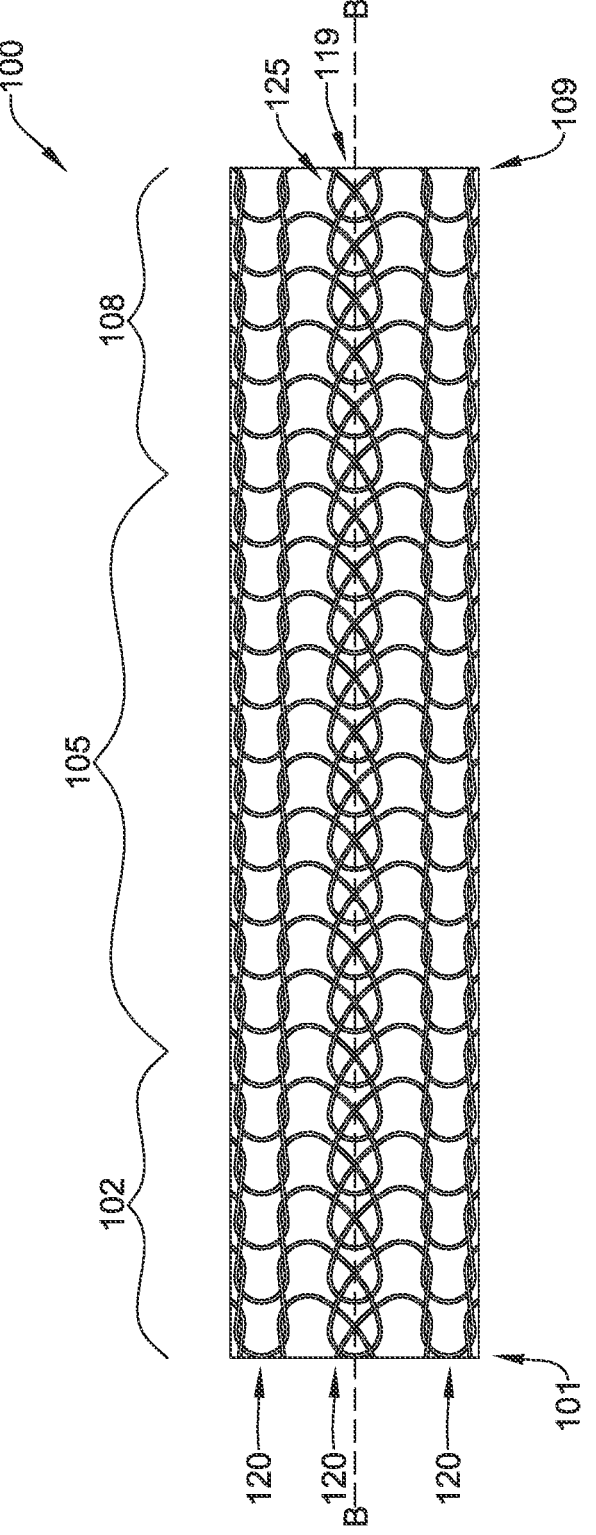
FIG. 7 is an illustration of a knitted stent including a row of twisted loops extending from a first end of the knitted stent to a second end of the knitted stent.

FIG. 7 is a side view illustrating a portion of one example of the knitted stent 100, which may include features as discussed above with respect to FIG. 5. In an alternative configuration, FIG. 7 may be considered to illustrate a portion of the knitted stent 200, which may include features as discussed above with respect to FIG. 6. For the purpose of brevity, the following discussion is directed toward the knitted stent 100, but such discussion is not intended to be limiting. The knitted stent 100 may include a first end portion 102 proximate and/or extending from a first end 101, a second end portion 108 proximate and/or extending from a second end 109, and a body portion 105 disposed axially and/or longitudinally between the first end portion 102 and the second end portion 108 along the central longitudinal axis B-B.

In at least some embodiments, the at least one of the plurality of loop rows 120 including the plurality of closed cells 125 may include a first loop row 119 extending within the first end portion 102, the body portion 105, and the second end portion 108 along and/or parallel to the central longitudinal axis B-B. In some embodiments, the first loop row 119 may extend from the first end 101 of the knitted stent 100 to the second end 109 of the knitted stent 100 along and/or parallel to the central longitudinal axis B-B. In some embodiments, at least some of the plurality of closed cells 125 may be interwoven and/or interlaced with each other within the first loop row 119. In some embodiments, the plurality of closed cells 125 may be arranged immediately adjacent to each other from the first end 101 of the knitted stent 100 to the second end 109 of the knitted stent 100 within the first loop row 119. In some embodiments, every closed cell within the knitted stent 100 may be disposed within the first loop row 119. In some embodiments, a sum of the plurality of cells of the plurality of loop rows 120 in the first end portion 102, the second end portion 108, and the body portion 105 may comprise at least 90% open cells.

In some embodiments, the plurality of closed cells 125 (e.g., the twisted loops) may exert a circumferential force on the first end portion 102, the body portion 105, and/or the second end portion 108 of the knitted stent 100. In some embodiments, the plurality of closed cells 125 (e.g., the twisted loops) may allow a consistent radial force to be exerted on the first end portion 102, the body portion 105, and/or the second end portion 108 of the knitted stent 100 while maintaining an optional circumferential expansion that is appropriate to the vessel dimensions associated with the first end portion 102, the body portion 105, and/or the second end portion 108 of the knitted stent 100, which may be similar or different depending on the anatomical variation.

Figure 8A:
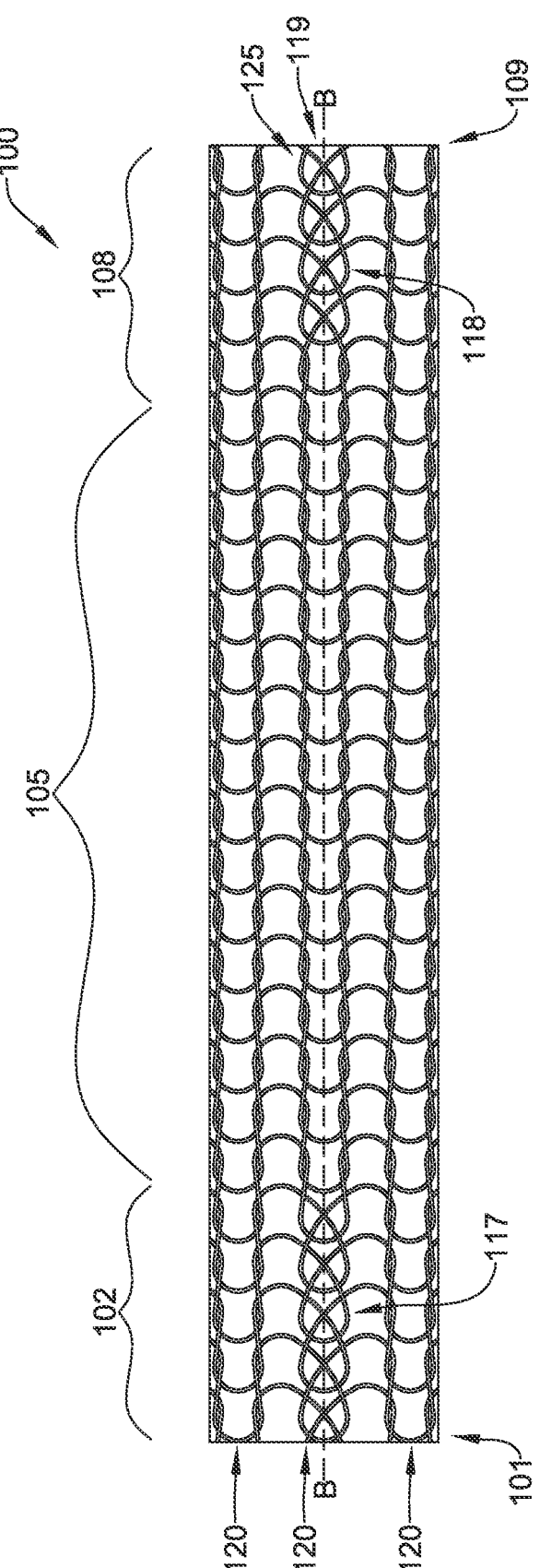
FIG. 8A is an illustration of a knitted stent including a row of twisted loops extending within a first end portion and a second end portion of the knitted stent.

FIG. 8A is a side view illustrating a portion of another example of the knitted stent 100, which may include features as discussed above with respect to FIG. 5. In an alternative configuration, FIG. 8A may be considered to illustrate a portion of the knitted stent 200, which may include features as discussed above with respect to FIG. 6. For the purpose of brevity, the following discussion is directed toward the knitted stent 100, but such discussion is not intended to be limiting. The knitted stent 100 may include a first end portion 102 proximate and/or extending from a first end 101, a second end portion 108 proximate and/or extending from a second end 109, and a body portion 105 disposed axially and/or longitudinally between the first end portion 102 and the second end portion 108 along the central longitudinal axis B-B.

In some embodiments, within the body portion 105, the plurality of loop rows 120 may be formed completely and/or entirely from open cells having an open end 123 disposed between the two longitudinally oriented connector elements 124 and opposite the circumferential loop element 122 (e.g., FIG. 5). In some embodiments, within the first end portion 102, at least one of the plurality of loop rows 120 includes a first plurality of closed cells having a closed end 127 formed by crossing the two longitudinally oriented connector elements 124 at a position opposite the circumferential loop element 122 (e.g., FIG. 5). In some embodiments, within the second end portion 108, at least one of the plurality of loop rows 120 includes a second plurality of closed cells having a closed end 127 formed by crossing the two longitudinally oriented connector elements 124 at a position opposite the circumferential loop element 122 (e.g., FIG. 5).

In at least some embodiments, the at least one of the plurality of loop rows 120 including the plurality of closed cells 125 may include a first portion of a first loop row 119 and a second portion of the first loop row 119 spaced apart axially and/or longitudinally from the first portion. In some embodiments, the first portion of the first loop row 119 may extend and/or be disposed within the first end portion 102 along and/or parallel to the central longitudinal axis B-B. In some embodiments, the second portion of the first loop row 119 may extend and/or be disposed within the second end portion 108 along and/or parallel to the central longitudinal axis B-B. The first end portion 102 and the second end portion 108 may be spaced apart by the body portion 105 of the knitted stent 100.

Figure 8B:
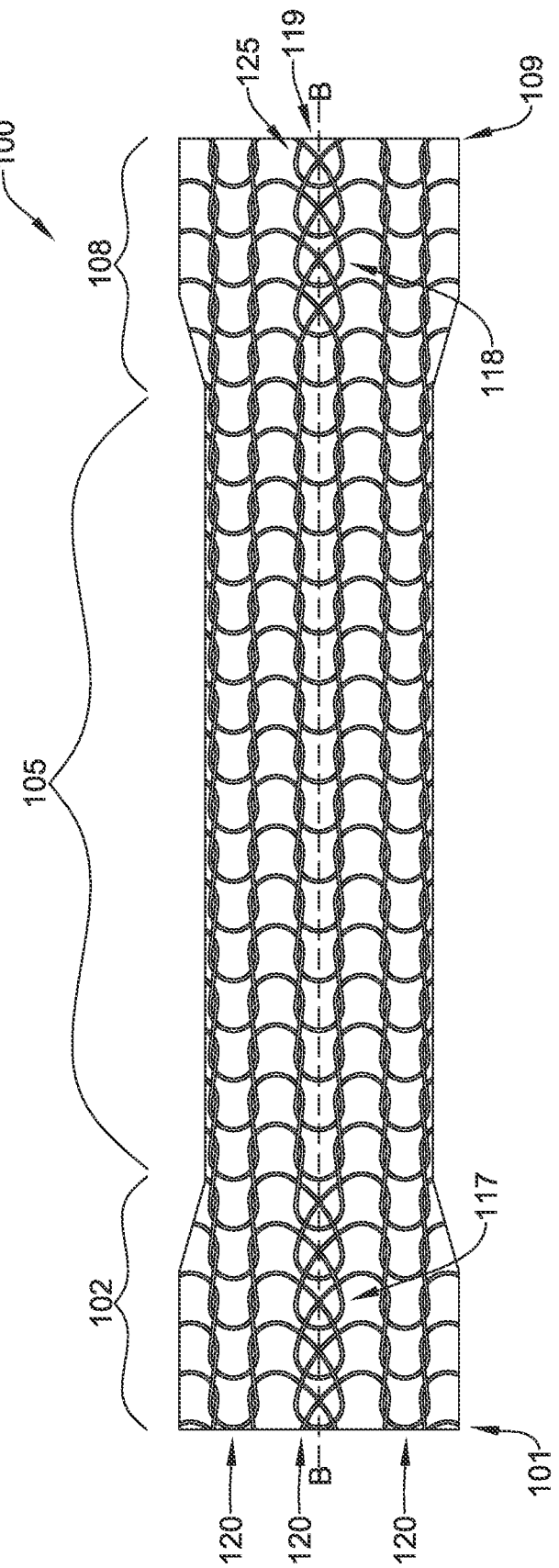
FIG. 8B is an illustration of a knitted stent with flared ends including a row of twisted loops extending within a first flared end portion and a second flared end portion of the knitted stent.

As may be seen in FIG. 8B, in some embodiments, the first end portion 102 and the second end portion 108 may each have an outer diameter that is greater than an outer diameter of the body portion 105. In some embodiments, in the radially expanded configuration of the knitted stent 100, the first end portion 102 may have a first outer diameter greater than the outer diameter of the body portion 105. In such embodiments, the first end portion 102 may be considered and/or referred to as a first flared end portion. In some embodiments, in the radially expanded configuration of the knitted stent 100, the second end portion 108 may have a second outer diameter greater than the outer diameter of the body portion 105. In such embodiments, the second end portion 108 may be considered and/or referred to as a second flared end portion. In some embodiments, the first outer diameter may be the same as the second outer diameter. In some embodiments, the first outer diameter may be different from the second outer diameter. In the example of FIG. 8B, the first outer diameter and the second outer diameter are both different from the outer diameter of the body portion 105. In the example of FIG. 8A, the first outer diameter and the second outer diameter are both substantially identical to (e.g., the same as) the outer dimeter of the body portion 105. Other configurations are also contemplated. For example, the first outer diameter of the first end portion 102 may be greater than the outer diameter of the body portion 105 and the second outer diameter of the second end portion 108 may be substantially identical to the outer diameter of the body portion 105, or vice versa.

With respect to the example configurations of both FIG. 8A and FIG. 8B, in some embodiments, the first portion of the first loop row 119 may extend from the body portion 105 toward and/or to the first end 101 of the knitted stent 100 along and/or parallel to the central longitudinal axis B-B, and the second portion of the first loop row 119 may extend from the body portion 105 toward and/or to the second end 109 of the knitted stent 100 along and/or parallel to the central longitudinal axis B-B. In some embodiments, the first portion may include a first plurality of closed cells 117 and the second portion may include a second plurality of closed cells 118. In some embodiments, the plurality of closed cells 125 (e.g., the twisted loops) described herein may include the first plurality of closed cells 117 and/or the second plurality of closed cells 118, and characteristics and/or features of each may be used and/or applied interchangeably, unless expressly specified otherwise.

In some embodiments, the first plurality of closed cells 117 may be interwoven and/or interlaced with each other within the first loop row 119. In some embodiments, the second plurality of closed cells 118 may be interwoven and/or interlaced with each other within the first loop row 119. In some embodiments, the first plurality of closed cells 117 may extend and/or may be arranged immediately adjacent to each other from the body portion 105 to the first end 101 of the knitted stent 100 along the central longitudinal axis B-B and/or within the first loop row 119. In some embodiments, the second plurality of closed cells 118 may extend and/or may be arranged immediately adjacent to each other from the body portion 105 to the second end 109 of the knitted stent 100 along the central longitudinal axis B-B and/or within the first loop row 119. In some embodiments, every closed cell within the knitted stent 100 may be disposed within the first loop row 119. In some embodiments, a sum of the plurality of cells of the plurality of loop rows 120 in the first end portion 102, the second end portion 108, and the body portion 105 may comprise at least 90% open cells.

In some embodiments, the first plurality of closed cells 117 (e.g., the twisted loops) may exert a first circumferential force on the first end portion 102 of the knitted stent 100. In some embodiments, the second plurality of closed cells 118 (e.g., the twisted loops) may exert a second circumferential force on the second end portion 108 of the knitted stent 100. In some embodiments, the first circumferential force may be substantially identical to the second circumferential force. In some embodiments, the first circumferential force may be different from the second circumferential force. For example, in some embodiments, the first circumferential force may be greater than the second circumferential force, or vice versa. In some embodiments, the first plurality of closed cells 117 (e.g., the twisted loops) may allow a consistent radial force to be exerted on the first end portion 102 of the knitted stent 100 while maintaining an optional circumferential expansion that is appropriate to the vessel dimensions associated with the first end portion 102 of the knitted stent 100, which may be similar or different depending on the anatomical variation. In some embodiments, the second plurality of closed cells 118 (e.g., the twisted loops) may allow a consistent radial force to be exerted on the second end portion 108 of the knitted stent 100 while maintaining an optional circumferential expansion that is appropriate to the vessel dimensions associated with the second end portion 108 of the knitted stent 100, which may be similar or different depending on the anatomical variation.

The first flared end portion and/or the second flared end portion may be configured to engage the wall of the body lumen. It is contemplated that a transition from the body portion to the first flared end portion and/or the second flared end portion may be gradual, sloped, or occur in an abrupt stepwise manner, as desired. In some embodiments, the outer diameter of the body portion may be in the range of about 15 millimeters to about 25 millimeters. In some embodiments, the first outer diameter of the first flared end portion and/or the second outer diameter of the second flared end portion may be in the range of about 20 millimeters to about 30 millimeters. It is contemplated that the outer diameter of the knitted stent 100 may be varied to suit the desired application.

Figure 9A:
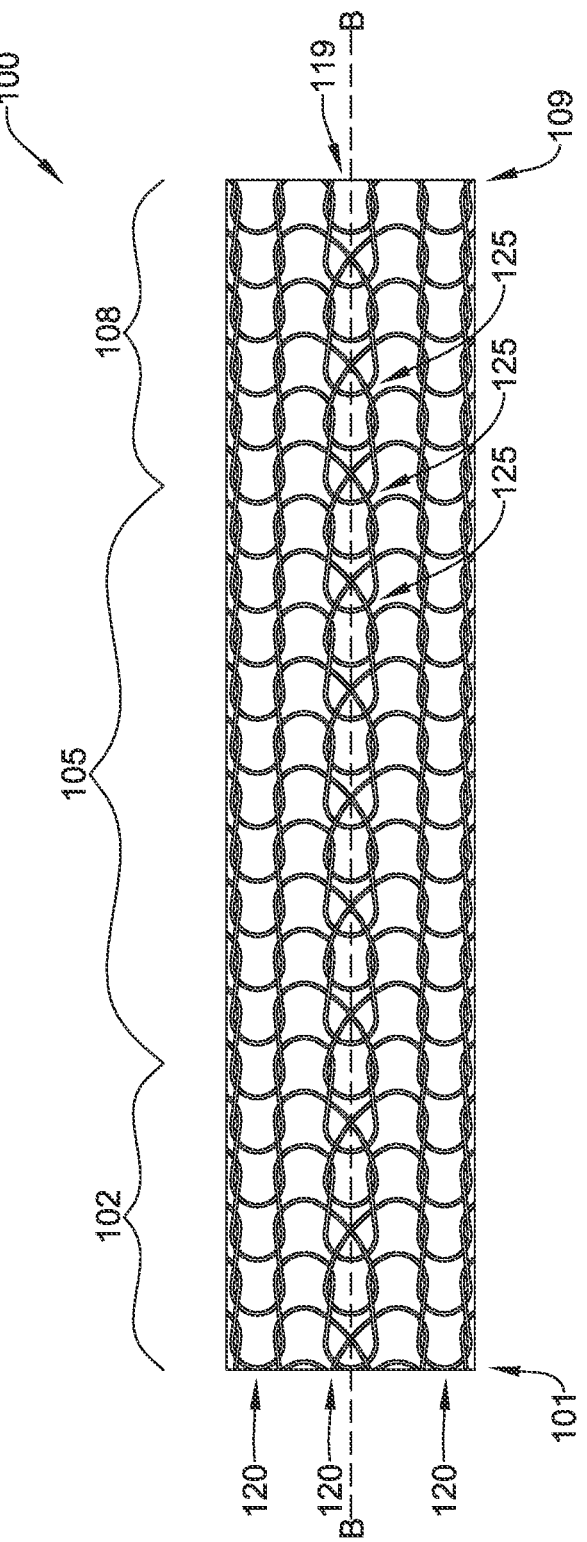
FIG. 9A is an illustration of a portion of a knitted stent including a row having a pattern of twisted loops alternating every other column with open loops.
Figure 9B:
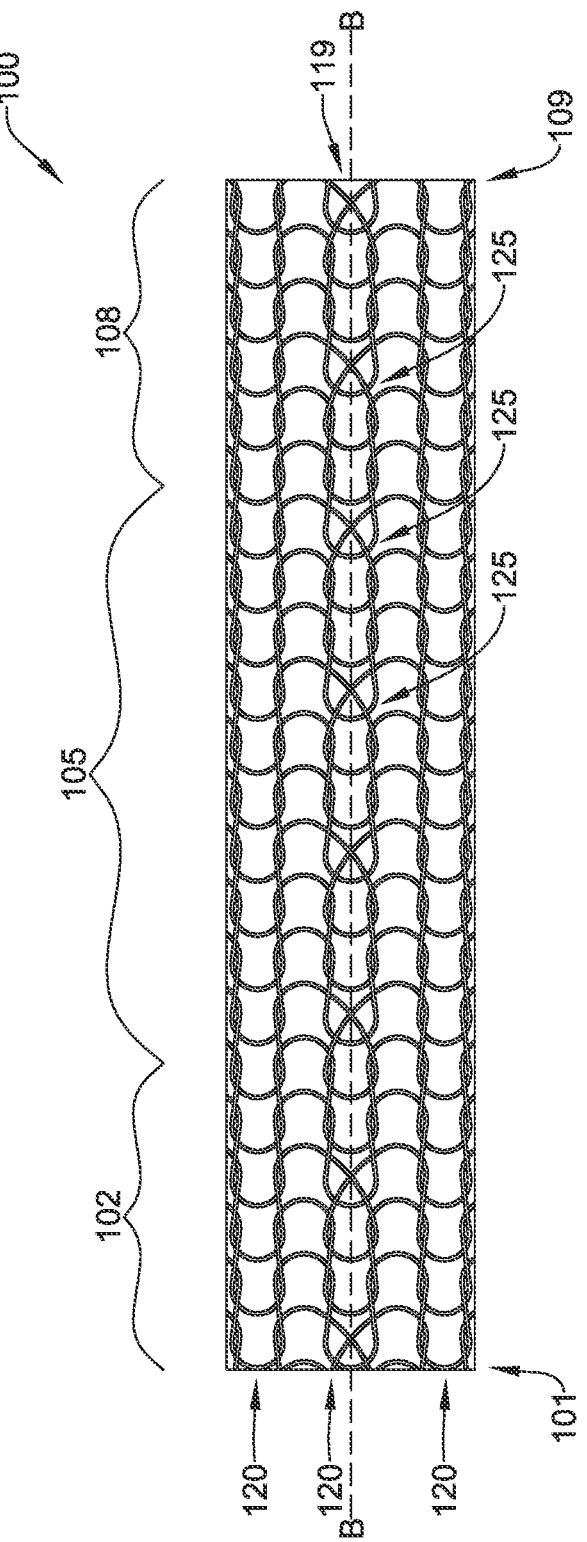
FIG. 9B is an illustration of a portion of a knitted stent including a row having a pattern of twisted loops disposed at every third column with two columns of open loops therebetween.

FIGS. 9A and 9B are side views illustrating a portion of alternative configurations of the knitted stent 100 of FIG. 7. Alternatively, FIGS. 9A and 9B may be considered to illustrate a portion of the knitted stent 200. For the purpose of brevity, the following discussion is directed toward the knitted stent 100, but such discussion is not intended to be limiting. The knitted stent 100 may include a first end portion 102 proximate and/or extending from a first end 101, a second end portion 108 proximate and/or extending from a second end 109, and a body portion 105 disposed axially and/or longitudinally between the first end portion 102 and the second end portion 108 along the central longitudinal axis B-B.

In some embodiments, a majority of the plurality of loop rows 120 include open cells having an open end 123 disposed between the two longitudinally oriented connector elements 124 and opposite the circumferential loop element 122 (e.g., FIG. 5). At least one of the plurality of loops rows 120 includes a plurality of closed cells 125 having a closed end 127 formed by crossing the two longitudinally oriented connector elements 124 at a position opposite the circumferential loop element 122 (e.g., FIG. 5). In some embodiments, the at least one of the plurality of loop rows 120 including the plurality of closed cells 125 may include a first loop row 119 extending within the first end portion 102, the body portion 105, and the second end portion 108 along and/or parallel to the central longitudinal axis B-B. In some embodiments, the first loop row 119 may extend from the first end 101 of the knitted stent 100 to the second end 109 of the knitted stent 100 along and/or parallel to the central longitudinal axis B-B.

In some embodiments, at least some of the plurality of closed cells 125 may be interwoven and/or interlaced with open cells within the first loop row 119. For example, in some embodiments, the plurality of closed cells 125 is longitudinally spaced apart from each other within the at least one of the plurality of loops rows 120 and/or within the first loop row 119. In some embodiments, the plurality of closed cells 125 is longitudinally spaced apart from each other from the first end 101 of the knitted stent 100 to the second end 109 of the knitted stent 100 within the first loop row 119. In some embodiments, each consecutive pair of the plurality of closed cells 125 may be spaced longitudinally apart from each other by one open cell within the at least one of the plurality of loops rows 120 and/or within the first loop row 119, as shown in FIG. 9A. In some embodiments, each consecutive pair of the plurality of closed cells 125 may be spaced longitudinally apart from each other by two open cells within the at least one of the plurality of loops rows 120 and/or within the first loop row 119, as shown in FIG. 9B. Other configurations are also contemplated. In some embodiments, every closed cell within the knitted stent 100 may be disposed within the first loop row 119. In some embodiments, a sum of the plurality of cells of the plurality of loop rows 120 in the first end portion 102, the second end portion 108, and the body portion 105 may comprise at least 90% open cells.

The materials that can be used for the various components of the knitted stent 100/200 and the various elements thereof disclosed herein may include those commonly associated with medical devices. For simplicity purposes, the following discussion makes reference to the knitted stent 100/200. However, this is not intended to limit the devices and methods described herein, as the discussion may be applied to other elements, members, components, or devices disclosed herein, such as, but not limited to, the expandable framework, the anchoring portion, the body portion, the linking portion, the polymeric cover, and/or elements or components thereof.

In some embodiments, the knitted stent 100/200, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In some embodiments, a linear elastic and/or non-superelastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the knitted stent 100/200, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the endoprosthesis 100/200 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the endoprosthesis 100/200 to achieve the same result.

In some embodiments, a degree of Magnetic Resonance Imaging (MRI) compatibility is imparted into the knitted stent 100/200 and/or other elements disclosed herein. For example, the knitted stent 100/200, and/or components or portions thereof, may be made of a material that does not substantially distort the image and create substantial artifacts (i.e., gaps in the image). Certain ferromagnetic materials, for example, may not be suitable because they may create artifacts in an MRI image. The knitted stent 100/200, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOXR, and the like), nickel-cobalt-chromium-molybdenum alloys (e.g., UNS: R30035 such as MP35-NR and the like), nitinol, and the like, and others.

In some embodiments, the knitted stent 100/200 and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the knitted stent 100/200 and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum, or a Ni—Co—Cr-based alloy. The yarns may further include carbon, glass, or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the knitted stent 100/200 and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl-ketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine);

anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A knitted stent extending along a central longitudinal axis, comprising:

a filament forming a plurality of cells arranged in a plurality of columns and a plurality of rows;

wherein the plurality of rows extends parallel to the central longitudinal axis from a first end of the knitted stent to a second end of the knitted stent;

wherein the plurality of columns extends circumferentially around the central longitudinal axis;

wherein the plurality of rows includes a plurality of loop rows and a plurality of rung rows interposed between adjacent loop rows;

wherein each cell within the plurality of loop rows includes a circumferential loop element connected to two longitudinally oriented connector elements;

wherein the plurality of rung rows includes a plurality of circumferential rung elements having opposite ends connected to adjacent loop rows;

wherein the knitted stent includes a first end portion, a second end portion, and a body portion disposed between the first end portion and the second end portion;

wherein in a radially expanded configuration, the first end portion and the second end portion each have an outer diameter that is greater than an outer diameter of the body portion;

wherein within the body portion, the plurality of loop rows is formed from open cells having an open end disposed between the two longitudinally oriented connector elements and opposite the circumferential loop element;

wherein within the first end portion, at least one of the plurality of loop rows includes a first plurality of closed cells having a closed end formed by crossing the two longitudinally oriented connector elements at a position opposite the circumferential loop element, wherein the first plurality of closed cells are each in a circumferential column with a plurality of open cells;

wherein within the second end portion, at least one of the plurality of loop rows includes a second plurality of closed cells having a closed end formed by crossing the two longitudinally oriented connector elements at a position opposite the circumferential loop element, wherein the second plurality of closed cells are each in a circumferential column with a plurality of open cells.

2. The knitted stent of claim 1, wherein a sum of the plurality of cells of the plurality of loop rows in the first end portion, the second end portion, and the body portion comprises at least 90% open cells.

3. The knitted stent of claim 1, wherein the first plurality of closed cells extends from the body portion to the first end of the knitted stent and the second plurality of closed cells extends from the body portion to the second end of the knitted stent.

4. The knitted stent of claim 1, wherein the circumferential loop element of at least some of the first plurality of closed cells and the second plurality of closed cells extends behind the closed end of a closed cell in an adjacent column.

5. The knitted stent of claim 1, wherein every closed cell of the knitted stent is disposed within a single loop row.

6. The knitted stent of claim 5, wherein each closed cell of the first plurality of closed cells is arranged immediately adjacent to each other.

7. The knitted stent of claim 5, wherein each closed cell of the second plurality of closed cells is arranged immediately adjacent to each other.

8. The knitted stent of claim 1, wherein the circumferential loop element of each cell is oriented toward the first end of the knitted stent.

9. The knitted stent of claim 1, wherein the plurality of circumferential rung elements is connected at opposite ends to one of the two longitudinally oriented connector elements from each adjacent loop row.

10. A knitted stent extending along a central longitudinal axis, comprising:

a filament forming a plurality of cells arranged in a plurality of columns and a plurality of rows;

wherein the plurality of rows extends parallel to the central longitudinal axis from a first end of the knitted stent to a second end of the knitted stent;

wherein the plurality of columns extends circumferentially around the central longitudinal axis;

wherein the plurality of rows includes a plurality of loop rows and a plurality of rung rows interposed between adjacent loop rows;

wherein each cell within the plurality of loop rows includes a circumferential loop element connected to two longitudinally oriented connector elements;

wherein the plurality of rung rows includes a plurality of circumferential rung elements connected to adjacent loop rows;

wherein a majority of the plurality of loop rows includes open cells having an open end disposed between the two longitudinally oriented connector elements and opposite the circumferential loop element;

wherein at least one of the plurality of loop rows includes a first plurality of closed cells having a closed end formed by crossing the two longitudinally oriented connector elements at a position opposite the circumferential loop element, the first plurality of closed cells being disposed adjacent the first end of the knitted stent, wherein the first plurality of closed cells are each in a circumferential column with a plurality of open cells;

wherein at least one of the plurality of loop rows includes a second plurality of closed cells having a closed end formed by crossing the two longitudinally oriented connector elements at a position opposite the circumferential loop element, the second plurality of closed cells being disposed adjacent the second end of the knitted stent, wherein the second plurality of closed cells are each in a circumferential column with a plurality of open cells;

wherein the first plurality of closed cells is longitudinally spaced apart from the second plurality of closed cells.

11. The knitted stent of claim 10, wherein each closed cell of the first plurality of closed cells is arranged immediately adjacent to each other.

12. The knitted stent of claim 10, wherein each closed cell of the second plurality of closed cells is arranged immediately adjacent to each other.

13. The knitted stent of claim 10, wherein every closed cell of the knitted stent is disposed within a single loop row.

14. The knitted stent of claim 10, wherein the circumferential loop element of each cell is oriented toward the first end of the knitted stent.

15. The knitted stent of claim 10, wherein the plurality of circumferential rung elements is connected at opposite ends to one of the two longitudinally oriented connector elements from each adjacent loop row.

16. A knitted stent extending along a central longitudinal axis, comprising:

a filament forming a plurality of cells arranged in a plurality of columns and a plurality of rows;

wherein the plurality of rows extends parallel to the central longitudinal axis from a first end of the knitted stent to a second end of the knitted stent;

wherein the plurality of columns extends circumferentially around the central longitudinal axis;

wherein the plurality of rows includes a plurality of loop rows and a plurality of rung rows interposed between adjacent loop rows;

wherein each cell within the plurality of loop rows includes a circumferential loop element connected to two longitudinally oriented connector elements;

wherein the plurality of rung rows includes a plurality of circumferential rung elements connected to adjacent loop rows;

wherein a majority of the plurality of loop rows includes open cells having an open end disposed between the two longitudinally oriented connector elements and opposite the circumferential loop element;

wherein the plurality of loop rows includes at least a first loop row and a second loop row circumferentially spaced apart from the first loop row;

wherein the first loop row includes a first portion disposed proximate the first end of the knitted stent and a second portion disposed proximate the second end of the knitted stent, wherein the second portion of the first loop row is spaced apart longitudinally from the first portion of the first loop row;

wherein the first portion of the first loop row includes a first plurality of closed cells having a closed end formed by crossing the two longitudinally oriented connector elements at a position opposite the circumferential loop element, and the second portion of the first loop row includes a second plurality of closed cells having a closed end formed by crossing the two longitudinally oriented connector elements at a position opposite the circumferential loop element, wherein the first plurality of closed cells and the second plurality of closed cells are each in a circumferential column with a plurality of open cells;

wherein the second loop row includes a first portion disposed proximate the first end of the knitted stent and a second portion disposed proximate the second end of the knitted stent, wherein the second portion of the second loop row is spaced apart longitudinally from the first portion of the second loop row;

wherein the first portion of the second loop row includes a first plurality of closed cells having a closed end formed by crossing the two longitudinally oriented connector elements at a position opposite the circumferential loop element, and the second portion of the second loop row includes a second plurality of closed cells having a closed end formed by crossing the two longitudinally oriented connector elements at a position opposite the circumferential loop element.

17. The knitted stent of claim 16, wherein the first plurality of closed cells in the first loop row is arranged immediately adjacent to each other along the central longitudinal axis and the second plurality of closed cells in the first loop row is arranged immediately adjacent to each other along the central longitudinal axis.

18. The knitted stent of claim 16, wherein the first plurality of closed cells in the second loop row is arranged immediately adjacent to each other along the central longitudinal axis and the second plurality of closed cells in the second loop row is arranged immediately adjacent to each other along the central longitudinal axis.

19. The knitted stent of claim 16, wherein the first portion of the first loop row and the first portion of the second loop row are disposed within a first end portion of the knitted stent, and the second portion of the first loop row and the second portion of the second loop row are disposed within a second end portion of the knitted stent, wherein the first end portion and the second end portion are spaced apart by a body portion of the knitted stent.

20. The knitted stent of claim 19, wherein in a radially expanded configuration of the knitted stent, the first end portion has a first outer diameter greater than an outer diameter of the body portion, and the second end portion has a second outer diameter greater than an outer diameter of the body portion.

* * * * *